(12) United States Patent
Tsao et al.

(10) Patent No.: US 10,809,534 B2
(45) Date of Patent: Oct. 20, 2020

(54) PHOTOGRAPHY DEVICE

(71) Applicant: Faspro Systems Co., Ltd., Taipei (TW)

(72) Inventors: Steve Tsao, Taipei (TW); Yi-Hung Chu, Taipei (TW); Shih-Hua Yu, Taipei (TW); Pao-Chyuan Chen, Taipei (TW); Wen-Kuang Hsieh, Taipei (TW); Ying-Hung Chen, Taipei (TW)

(73) Assignee: FASPRO SYSTEMS CO., LTD., Taipei (TW)

( * ) Notice: Subject to any disclaimer, the term of this patent is extended or adjusted under 35 U.S.C. 154(b) by 0 days.

(21) Appl. No.: 16/695,198

(22) Filed: Nov. 26, 2019

(65) Prior Publication Data

US 2020/0174256 A1   Jun. 4, 2020

Related U.S. Application Data

(60) Provisional application No. 62/773,200, filed on Nov. 30, 2018.

(30) Foreign Application Priority Data

Oct. 15, 2019 (TW) .............................. 108137124 A

(51) Int. Cl.
*H04N 5/232* (2006.01)
*G02B 27/01* (2006.01)
*A61B 90/00* (2016.01)

(52) U.S. Cl.
CPC ........ *G02B 27/0172* (2013.01); *A61B 90/361* (2016.02); *H04N 5/232121* (2018.08); *G02B 2027/014* (2013.01); *G02B 2027/0178* (2013.01)

(58) Field of Classification Search
CPC .......... H04N 5/232121; G02B 27/0172; G02B 2027/014; G02B 2027/0178; A61B 90/361
USPC ........................................................ 348/77
See application file for complete search history.

(56) References Cited

U.S. PATENT DOCUMENTS

| | | | | |
|---|---|---|---|---|
| 4,939,533 A | * | 7/1990 | Okada ....................... | G02B 7/32 396/120 |
| 5,652,927 A | * | 7/1997 | McIntyre .................. | G02B 7/28 396/108 |
| 5,737,085 A | * | 4/1998 | Zollars .................. | G01B 11/026 356/237.2 |
| 8,107,056 B1 | * | 1/2012 | Riza .......................... | G01C 3/32 356/4.05 |
| 2006/0077258 A1 | * | 4/2006 | Allen ..................... | G01S 3/7864 348/169 |
| 2007/0268575 A1 | | 11/2007 | Yamazaki | |
| 2009/0060487 A1 | * | 3/2009 | Lee .......................... | G03B 3/10 396/104 |
| 2012/0200686 A1 | | 8/2012 | Yu et al. | |

(Continued)

*Primary Examiner* — Michael Lee
(74) *Attorney, Agent, or Firm* — CKC & Partners Co., LLC

(57) ABSTRACT

A photography device includes a light transmitter, a light receiver, a processor, an adjustable focusing lens, and a driving module. The light transmitter is configured to transmit light to an object. The light receiver is configured to receive the reflected light. The processor is configured to generate a driving value according to transmission and reception of the light. The adjustable focusing lens has a focal length. The driving module is configured to adjust the focal length by driving the adjustable focusing lens according to the driving value.

8 Claims, 3 Drawing Sheets

(56) References Cited

U.S. PATENT DOCUMENTS

2014/0183264 A1\* 7/2014 Nunnink ................. G02B 3/14
235/462.24

\* cited by examiner

PHOTOGRAPHY DEVICE

RELATED APPLICATIONS

This application claims priority to U.S. Provisional Application Ser. No. 62/773,200, filed Nov. 30, 2018, and Taiwan Application Serial Number 108137124, filed Oct. 15, 2019, the disclosures of which are incorporated herein by reference in their entireties.

BACKGROUND

Technical Field

The present disclosure relates to a photography device.

Description of Related Art

In general, in order to provide medical teaching, live broadcasts for observation, and as evidence for future medical disputes, a photography unit is installed on the surgical lighting device to record the surgical procedure. However, since the distance between the photography unit installed on the surgical lighting device and the surgical site is relatively long, and the line of sight of the photography unit is easily blocked by the head of the medical staff, there is often a problem that it is difficult to maintain good photographing quality.

In view of this, there is a glasses type photographic equipment in which a camera is placed on an eyeglasses structure and worn by a doctor performing surgery. In this way, the camera is parallel to the doctor's line of sight, so that a better quality image can be recorded. In general, in order to provide a clear image, such a photographic equipment usually has a wider angle of view and does not require focusing. However, although such a method can make each part of the image substantially clear, if the image is enlarged locally to further view a specific part, the enlarged part will be limited by the factor of resolution and cannot present the image details clearly.

Accordingly, how to provide a photography device to solve the aforementioned problems becomes an important issue to be solved by those in the industry.

SUMMARY

An aspect of the disclosure is to provide a photography device that can solve the aforementioned problems.

According to an embodiment of the disclosure, a photography device includes a light transmitter, a light receiver, a processor, an adjustable focusing lens, and a driving module. The light transmitter is configured to transmit light to an object. The light receiver is configured to receive the reflected light. The processor is configured to generate a driving value according to transmission and reception of the light. The adjustable focusing lens has a focal length. The driving module is configured to adjust the focal length by driving the adjustable focusing lens according to the driving value.

In an embodiment of the disclosure, the processor is configured to generate a distance value according to the transmission and reception of the light, and configured to generate the driving value according to the distance value.

In an embodiment of the disclosure, the adjustable focusing lens has a working range. The processor is configured to generate the driving value according to the distance value only when the distance value is within the working range.

In an embodiment of the disclosure, the processor is further configured to generate the driving value according to a voltage-range of depth of field lookup table, such that the distance value is substantially at the center of a range of depth of field to which the driving value corresponds. In other words, the processor is further configured to generate the driving value according to the relationship between an applied voltage and a resulting clear range of view, such that the object is substantially at the center of the clear range of view to which the driving value corresponds.

In an embodiment of the disclosure, the light receiver is configured to correspondingly generate an electrical signal when receiving the reflected light. The processor is further configured to filter out noise in the electrical signal.

In an embodiment of the disclosure, the adjustable focusing lens is a liquid lens.

In an embodiment of the disclosure, the photography device further includes a light indicating module configured to emit an indicator light to the object.

In an embodiment of the disclosure, the light indicating module includes an indicator light source and a focusing lens. The indicator light source is configured to emit the indicator light. The focusing lens is configured to focus the indicator light.

In an embodiment of the disclosure, the photography device further includes an image sensor configured to sense an image of the object via the adjustable focusing lens. The processor is further configured to generate a cropped image according to an illumination range of the indicator light in the image.

In an embodiment of the disclosure, the photography device further includes an image sensor configured to sense an image of the object via the adjustable focusing lens.

In an embodiment of the disclosure, the photography device further includes a lens group optically coupled between the adjustable focusing lens and the image sensor. The image is optically magnified by the lens group.

Accordingly, the photography device of the present disclosure adopts an optically magnified viewing angle and cooperates with a fast dynamic autofocus technology to obtain an image of a local part intended to be taken by a user, and this image allows the user to obtain clear and high resolution image details. The photography device of the present disclosure further includes the light indicating module to facilitate indicating whether the position at which the user's photography device is currently photographing is the portion intended to be photographed.

It is to be understood that both the foregoing general description and the following detailed description are by examples, and are intended to provide further explanation of the disclosure as claimed.

BRIEF DESCRIPTION OF THE DRAWINGS

The disclosure can be more fully understood by reading the following detailed description of the embodiment, with reference made to the accompanying drawings as follows.

DETAILED DESCRIPTION

Figure 1:
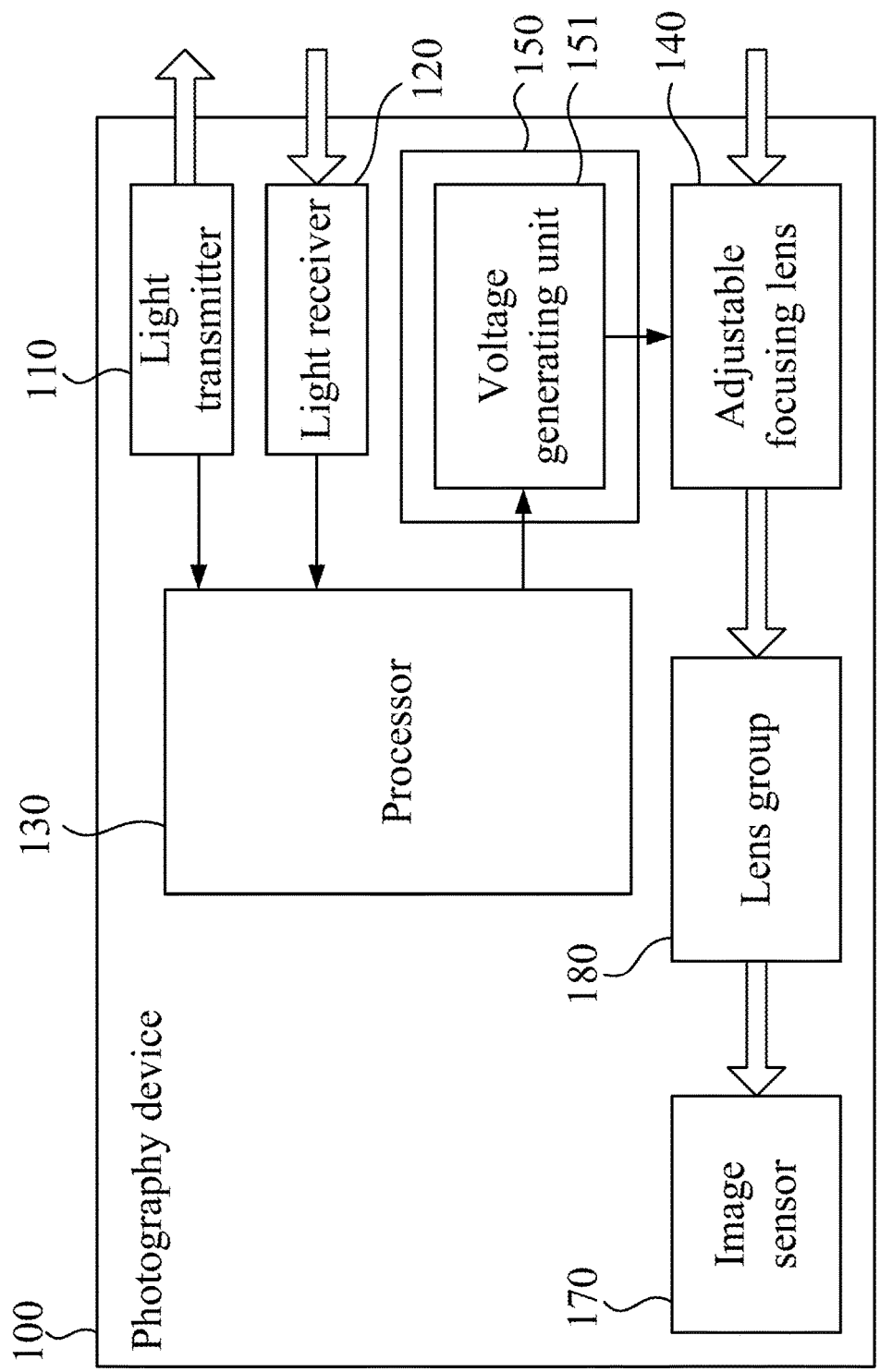
FIG. 1 is a functional block diagram of a photography device according to an embodiment of the disclosure.

Reference will now be made in detail to the present embodiments of the disclosure, examples of which are illustrated in the accompanying drawings. Wherever possible, the same reference numbers are used in the drawings and the description to refer to the same or like parts.

Reference is made to FIG. 1. FIG. 1 is a functional block diagram of a photography device 100 according to an embodiment of the disclosure. As shown in FIG. 1, in the present embodiment, the photography device 100 includes a light transmitter 110, a light receiver 120, a processor 130, an adjustable focusing lens 140, and a driving module 150. The light transmitter 110 is configured to transmit light to an object. The light receiver 120 is configured to receive the reflected light. The processor 130 is configured to generate a driving value according to transmission and reception of the light. The adjustable focusing lens 140 has a focal length. The driving module 150 is configured to adjust the focal length by driving the adjustable focusing lens 140 according to the driving value. In some embodiments, the driving value is a voltage value, but the disclosure is not limited in this regard.

In some embodiments, the photography device 100 further includes an image sensor 170 and a lens group 180. The image sensor 170 is configured to sense an image of the object via the adjustable focusing lens 140. The lens group 180 is optically coupled between the adjustable focusing lens 140 and the image sensor 170.

In some embodiments, the lens group 180 includes a plurality of lenses. The function of these lenses is to provide an optically magnified image viewing angle with a long depth of field (DOF). In some embodiments, each die of the adopted image sensor 170 has a larger image sensing area to reduce the impact of noise.

With the foregoing structural configurations, the photography device 100 of the present embodiment can adopt an optically magnified viewing angle and cooperate with a fast dynamic autofocus technology to obtain an image of a local part intended to be taken by a user, and this image allows the user to obtain clear and high resolution image details.

In some embodiments, the light transmitter 110 is a laser emitter, and the light receiver 120 is a laser receiver, but the disclosure is not limited in this regard. In some other embodiments, the light transmitter 110 is an infrared emitter, and the light receiver 120 is an infrared receiver.

In some embodiments, the driving module 150 is configured to drive the adjustable focusing lens 140 using the driving value. Specifically, in some embodiments, the driving module 150 includes a voltage generating unit 151. The voltage generating unit 151 is configured to drive the adjustable focusing lens 140 using the foregoing driving value. Specifically, the voltage generating unit 151 generates a voltage according to the foregoing driving value to drive the adjustable focusing lens 140.

In some embodiments, the processor 130 generates a distance value according to the timing at which the light transmitter 110 emits light and the timing at which the light receiver 120 receives the light. For example, the processor 130 can instantly calculate the distance value according to a time difference between the timing at which the light transmitter 110 emits the light and the timing at which the light receiver 120 receives the light according to a predetermined algorithm. In some other embodiments, the processor 130 can also obtain the distance value to which the foregoing time difference corresponds according to a predetermined time difference-distance lookup table.

In some embodiments, the processor 130 can further instantly convert the distance value into a corresponding driving value according to a predetermined algorithm. In some other embodiments, the processor 130 can also further obtain the driving value to which the foregoing distance value corresponds according to a predetermined distance-voltage lookup table. In some embodiments, the adjustable focusing lens 140 is a liquid lens. The liquid lens uses a liquid as a lens and changes the focal length by changing the curvature of the liquid. After the processor 130 generates the foregoing driving value, the voltage generating unit 151 generates a corresponding voltage according to the driving value corresponds to the adjustable focusing lens 140, that is, changes the shape of the adjustable focusing lens 140 in the way of the applied voltage, thereby changing the focal length thereof. As such, the photography device 100 of the present embodiment can automatically adapt to the distance of the object to be photographed without the assistance of a mechanical device, and the purpose of focusing can be achieved by simply changing the voltage between two electrodes to modify the shape of the adjustable focusing lens 140. Compared with the conventional lens, the photography device 100 of the present embodiment has the advantages of small size, low price, low power consumption, fast focusing speed, long life, and good image quality.

In some embodiments, the light receiver 120 can correspondingly generate an electrical signal when receiving the reflected light. The processor 130 is further configured to filter out noise in the electrical signal. For example, when the distance value generated by the processor 130 changes dramatically (e.g., from 30 cm to 3 cm), the processor 130 can filter out the drastically changed distance value without taking it. As such, the photography device 100 of the present embodiment prevents the adjustable focusing lens 140 from adjusting its focal length corresponding to the noise, thereby providing a better user experience.

In some embodiments, the adjustable focusing lens 140 has a working range. The processor 130 is configured to generate the driving value according to the distance value only when the distance value is within the working range. For example, the adjustable focusing lens 140 has a working range of about 4 cm to about 200 cm. When the distance value generated by the processor 130 is smaller than 3 cm which has exceeded the lower limit of the adjustable focal length of the adjustable focusing lens 140, the processor 130 does not need to generate a driving value according to the distance value. When the distance value generated by the processor 130 is greater than 200 cm which has exceeded the upper limit of the adjustable focal length of the adjustable focusing lens 140, the processor 130 also does not need to generate a driving value according to the distance value. As such, the photography device 100 of the present embodiment can drive the adjustable focusing lens 140 to adjust its focal length only when necessary, thereby reducing energy consumption and extending the life of the parts.

Figure 2:
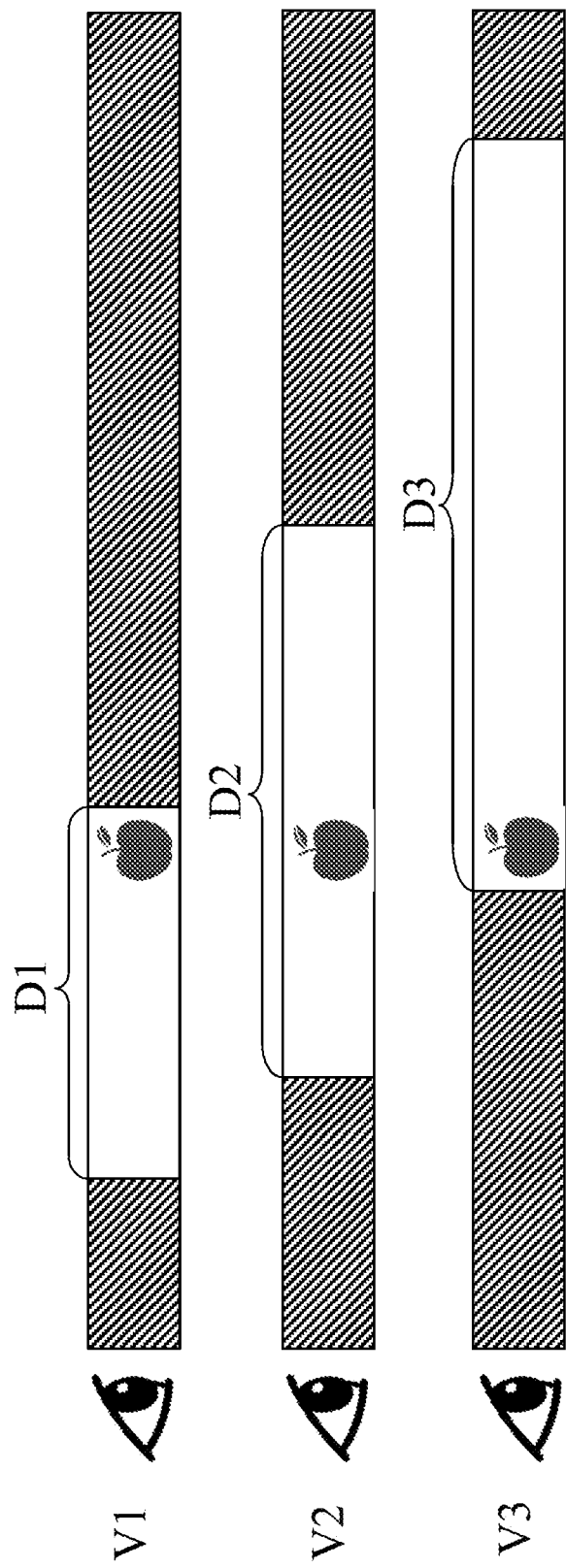
FIG. 2 is a diagram showing the relationship between the applied voltage and the resulting clear range of views of the photography device according to an embodiment of the disclosure.

Reference is made to FIG. 2. FIG. 2 is a diagram showing the relationship between the applied voltage and the resulting clear range of views of the photography device 100 according to an embodiment of the disclosure. As shown in FIG. 2, the object photographed by the photography device 100 of the present embodiment is exemplified by an apple. After the processor 130 generates the distance value, making the voltage generating unit 151 drive the adjustable focusing lens 140 by using any of voltage values V1, V2, V3, the resulting ranges D1, D2, D3 of DOF all cover the apple, thus obtaining a clear apple image. However, as shown in FIG. 2, when there is a small change in distance detection, the apple easily exceeds the range D1, D3 of DOF, so the voltage value V2 is obviously a better choice. Therefore, in some embodiments, the voltage value V2 generated by the processor 130 can cause the distance value to be substantially at the center of the range D2 of DOF. In practice, a complete voltage-range of DOF lookup table for photography device 100 can be obtained by systematic approach based on the above principles.

Figure 3:
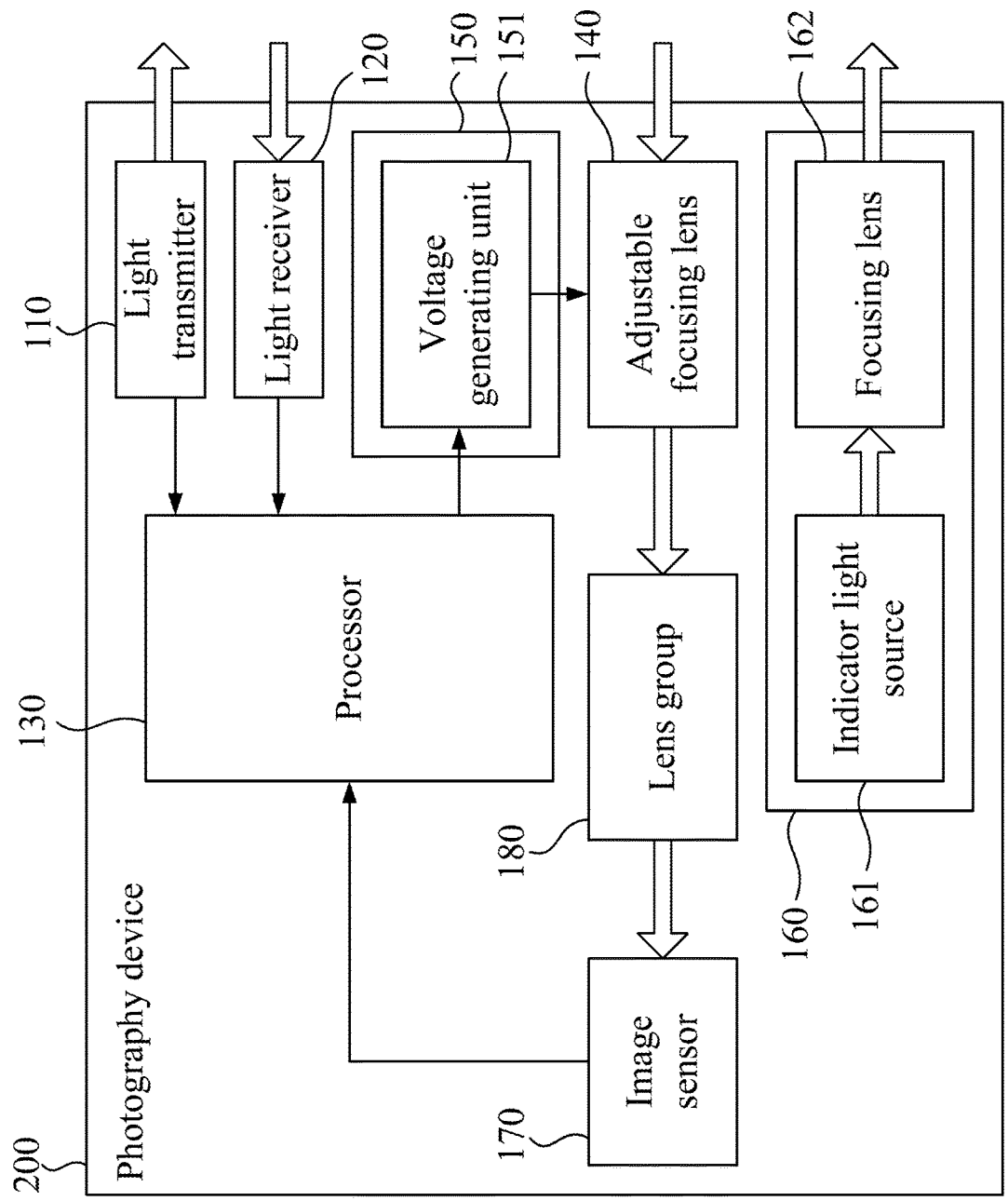
FIG. 3 is a functional block diagram of a photography device according to another embodiment of the disclosure.

Reference is made to FIG. 3. FIG. 3 is a functional block diagram of a photography device 200 according to another embodiment of the disclosure. Compared with the embodiment as shown in FIG. 1, the photography device 200 of the present embodiment further includes a light indicating module 160. The light indicating module 160 is configured to emit an indicator light to the object. Specifically, in some embodiments, the light indicating module 160 includes an indicator light source 161 and a focusing lens 162. The indicator light source 161 is configured to emit the indicator light. The focusing lens 162 is configured to focus the indicator light. Since the angle of beam of the indicator light passing through the focusing lens 162 is small, a focused radiography effect is generated, thereby facilitating the indication of whether the position photographed by the user's photography device 200 is a predetermined position (e.g., a surgical site).

In some embodiments, the indicator light source 161 is a light-emitting diode, but the disclosure is not limited in this regard. In practical applications, other similar light sources can be used.

In some embodiments, the distance between the light transmitter 110 and the camera lens (i.e., a combination of the adjustable focusing lens 140 and the lens group 180) of the photography device 200 can be reduced to reduce focusing error. In some embodiments, the distance between the light indicating module 160 and the camera lens of the photography device 200 can be reduced to reduce indicating error.

In some embodiments, the processor 130 is further configured to generate a cropped image according to an illumination range of the indicator light in the image. For example, when the object to be photographed is at the predefined working distance (e.g., 30 cm), the illumination range of the indicator light is at the center of the image, but when the object to be photographed is too close, the illumination range of the indicator light in the original image will be moved downward. At this time, the cropping range of the cropped image is also moved downward, so that the illumination range of the indicator light is still substantially at the center of the cropped image. As such, the photography device 200 of the present embodiment can automatically generate a clear image according to the illumination range of the indicator light. It should be noted that in order to perform the aforementioned cropping process, the size (sensing range) of the image sensor 170 needs to be larger than the image range to be displayed or stored.

According to the foregoing recitations of the embodiments of the disclosure, it can be seen that the photography device of the present disclosure adopts an optically magnified viewing angle and cooperates with a fast dynamic autofocus technology to obtain an image of a local part intended to be taken by a user, and this image allows the user to obtain clear and high resolution image details. The photography device of the present disclosure further includes the light indicating module to facilitate indicating whether the position at which the user's photography device is currently photographing is the portion intended to be photographed.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A photography device, comprising:
   a light transmitter configured to transmit light to an object;
   a light receiver configured to receive the reflected light;
   a processor configured to generate a driving value according to transmission and reception of the light;
   an adjustable focusing lens having a focal length;
   a driving module configured to adjust the focal length by driving the adjustable focusing lens according to the driving value;
   a light indicating module configured to emit an indicator light to the object; and
   an image sensor configured to sense an image of the object via the adjustable focusing lens, wherein the processor is further configured to generate a cropped image according to an illumination range of the indicator light in the image, so that the illumination range of the indicator light is at a center of the cropped image.

2. The photography device of claim 1, wherein the processor is configured to generate a distance value according to the transmission and reception of the light, and configured to generate the driving value according to the distance value.

3. The photography device of claim 2, wherein the adjustable focusing lens has a working range, and the processor is configured to generate the driving value according to the distance value only when the distance value is within the working range.

4. The photography device of claim 2, wherein the processor is further configured to generate the driving value according to a voltage-range of depth of field lookup table, such that the distance value is substantially at the center of a range of depth of field to which the driving value corresponds.

5. The photography device of claim 1, wherein the light receiver is configured to correspondingly generate an electrical signal when receiving the reflected light, and the processor is further configured to filter out noise in the electrical signal.

6. The photography device of claim 1, wherein the adjustable focusing lens is a liquid lens.

7. The photography device of claim 1, wherein the light indicating module comprises:
   an indicator light source configured to emit the indicator light; and
   a focusing lens configured to focus the indicator light.

8. The photography device of claim 1, further comprising a lens group optically coupled between the adjustable focusing lens and the image sensor, wherein the image is optically magnified by the lens group.

* * * * *